US007429466B2

(12) United States Patent
Wang

(10) Patent No.: US 7,429,466 B2
(45) Date of Patent: Sep. 30, 2008

(54) METHODS AND ARRAYS FOR DETECTING BIOLOGICAL MOLECULES

(75) Inventor: Yingjian Wang, Worcester, MA (US)

(73) Assignee: Hypromatrix, Inc, Worcester, MA (US)

( * ) Notice: Subject to any disclaimer, the term of this patent is extended or adjusted under 35 U.S.C. 154(b) by 623 days.

(21) Appl. No.: 10/173,991

(22) Filed: Jun. 18, 2002

(65) Prior Publication Data

US 2002/0155493 A1 Oct. 24, 2002

Related U.S. Application Data

(63) Continuation-in-part of application No. 09/767,538, filed on Jan. 23, 2001.

(60) Provisional application No. 60/326,311, filed on Oct. 1, 2001, provisional application No. 60/177,590, filed on Jan. 24, 2000.

(51) Int. Cl.
*G01N 1/30* (2006.01)
*G01N 33/53* (2006.01)

(52) U.S. Cl. .................. 435/40.51; 435/7.1; 435/7.2; 435/7.92; 435/40.5; 435/40.52

(58) Field of Classification Search .............. 435/6, 435/7.9, 40.51, 7.1, 7.2, 7.92, 40.5, 40.52
See application file for complete search history.

(56) References Cited

U.S. PATENT DOCUMENTS

| | | | |
|---|---|---|---|
| 4,750,100 A | 6/1988 | Ragsdale | |
| 4,910,140 A | 3/1990 | Dower | |
| 5,030,560 A * | 7/1991 | Sinor et al. ................ | 435/7.21 |
| 5,143,854 A | 9/1992 | Pirrung | |
| 5,149,655 A | 9/1992 | McCabe et al. | |
| 5,283,173 A | 2/1994 | Fields et al. | |
| 5,429,807 A | 7/1995 | Matson et al. | |
| 5,516,635 A | 5/1996 | Ekins et al. | |
| 5,616,745 A | 4/1997 | Behr et al. | |
| 5,702,896 A | 12/1997 | Collins et al. | |
| 5,744,305 A | 4/1998 | Fodor et al. | |
| 5,807,522 A | 9/1998 | Brown et al. | |
| 5,811,274 A | 9/1998 | Palsson | |
| 5,851,818 A | 12/1998 | Huang et al. | |
| 5,948,621 A * | 9/1999 | Turner et al. ................... | 435/6 |
| 6,180,348 B1 | 1/2001 | Li | |
| 6,197,506 B1 | 3/2001 | Fodor et al. | |
| 6,197,599 B1 * | 3/2001 | Chin et al. ................. | 436/518 |

OTHER PUBLICATIONS

Firth et al., Biotechniques vol. 23, No. 4 (1997) pp. 644-646.*
Kononen et al. Nature Medicine vol. 4, No. 7 (Jul. 1998) pp. 844-847.*
Wang et al., Immunostaining with dissociable antibody microarrays, Proteomics 2004, vol. 4, pp. 20-26.*
Chen et al., "High-Efficiency Transformation of Mammalian Cells by Plasmid DNA", *Molecular and Cellular Biology*, Aug. 1987, pp. 2745-2752.
Derise et al., "Use of a cDNA Microarray to Analyse Gene Expression Patterns in Human Cancer", *Nature Genetics*, Dec. 1996, vol. 14, pp. 457-460.
Dick et al., "Gene Transfer into Normal Human Hematopoietic Cells Using In Vitro and In Vivo Assays", *Blood*, Aug. 1, 1991, vol. 78, No. 3, pp. 624-634.
Felgner et al., "Lipofection: A Highly Efficient, Lipid-Mediated DNA-Transfection Procedure", *Proc. Natl. Acad. Sci USA*, Nov. 1987, vol. 84, pp. 7413-7417.
Firth et al., "Improved Procedure Electroporation of Peptides into Adherent Cells in Situ", *BioTechniques*, 1997, vol. 23, No. 4, pp. 644-646.
Fodor et al., "Light-Directed, Spatially Addressable Parallel Chemical Synthesis", *Science*, Feb. 15, 1991, vol. 251, pp. 767-773.
Gao et al., "Potentiation of Caitonic Liposome-Mediated Gene Delivery by Polycations", *Biochemistry*, 1996, vol. 35, No. 3, pp. 1027-1036.
"A Simple Procedure to Increase Efficiency Of DEAE-Dextran Transfection of COS Cells", *TIG*, Jun. 1995, vol. 11, No. 6, pp. 216-217.
Graham et al, "A New Technique for the Assay of Infectivity of Human Adenovirus 5 DNA", *Virology*, 1973, vol. 52, pp. 456-467.
Guesdon et al., "Magnetically Responsive Polyacrylamide Agarose Beads for the Preparation of Immunoabsorbents", *Journal of Immunological Methods*, 1978, vol. 21, pp. 59-63.
Hacia, J.G., "Resequencying and Mutational Analysis Using Oligonucleotide Microarrays", *Nature Genetics Supplement*, Jan. 1999, vol. 21, pp. 42-47.
Hofland et al., "Formation of Stable Cationic Lipid/DNA Complexes for Gene Transfer"; *Proc. Natl. Acad. Sci. USA*, Jul. 1996, vol. 93, pp. 7305-7309.
Kononen et al., "Tissue Microarrays for High-Throughput Molecular Profiling of Tumor Specimens", *Nature Medicine*, Jul. 1998, vol. 4, No. 7, pp. 844-847.

(Continued)

*Primary Examiner*—Mark L. Shibuya
(74) *Attorney, Agent, or Firm*—Mirick, O'Connell, DeMallie & Lougee, LLP

(57) ABSTRACT

Arrays and methods for detecting one or more biological molecules, where the methods generally comprise the steps of: providing a first support immobilized with one or more reagents; providing a second support immobilized with one or more of ligands; contacting the reagents immobilized to the first support with the ligands immobilized on the second support whereby one or more of the reagents bind to one or more of the ligands; and separating the first support from the second support so that one or more of the bound reagents remain bound to one or more ligands on the second support after separation. In one preferred method, proteins are immobilized on a support with adequate strength so that the proteins can be dissociated from the support under certain conditions, such as after binding with other proteins immobilized on another support. For example, antibody arrays produced according to the present invention may be used to detect protein expressions in a protein lysate and may be used in immunostaining to reveal the presence and location of proteins in cells.

21 Claims, 4 Drawing Sheets
(4 of 4 Drawing Sheet(s) Filed in Color)

OTHER PUBLICATIONS

Lehrach et al., "Hybridization Fingerprinting in Genome Mapping and Sequencing", *Genetic and Physical Mapping; Genome Analysis vol. 1: Genetic and Physical Mapping*, Cold Spring Harbor Laboratory Press, K.E. Davies & S.M. Tilghman, editors, 1990, pp. 39-81.

Liu et al., "Cationic Liposome-Mediated Intravenous Gene Delivery"; *The Journal of Biological Chemistry*, Oct. 20, 1995, vol. 270, No. 42, pp. 24864-24870.

Schena et al.,, "Quantitative Monitoring of Gene Expression Patterns with a Complementary DNA Microarray"; *Science*, Oct. 20, 1995, vol. 270, pp. 467-470.

Shigekawa et al., "Electroporation of Eukaryotes and Prokaryotes: A General Approach to the Introduction of Macromolecules into Cells"; *BioTechniques*, 1988, vol. 6, No. 8, pp. 742-751.

Ternynck et al., "Polyacrylamide-Protein Immunoadsorbents Prepared with Glutaraldehyde"; *Febs Letters*, Jun. 1972, vol. 23, No. 1, pp. 24-28.

Wigler et al., "DNA-Mediated Transfer of the Adenine Phosphoribosyltransferase Locus into Mammalian Cells"; *Proc. Natl. Acad. Sci. USA*, Mar. 1979, vol. 76, No. 3, 1373-1376.

Williams et al., "Introduction of Foreign Genes into Tissues of Living Mice by DNA-coated Microprojectiles"; *Proc. Natl. Acad. Sci. USA*, Apr. 1991, vol. 88, pp. 2726-2730.

Yang et al., "Efficient In Situ Electroporation of Mammalian Cells Grown on Microporous Membranes"; *Nucleic Acids Research*, 1995, vol. 23, No. 15, pp. 2803-2810.

Bordignon et al., "Gene Therapy in Peripheral Blood Lymphocytes and Bone Marrow for ADA Immunodeficient Patients"; *Science*, Oct. 20, 1995, vol. 270, pp. 470-475.

Bulyk et al., "Quantifying DNA-Protein Interactions by Double-Stranded DNA Arrays", *Nature Biotechnology*, Jun. 1999, vol. 17, pp. 573-577.

* cited by examiner

METHODS AND ARRAYS FOR DETECTING BIOLOGICAL MOLECULES

CROSS-REFERENCE

This application claims priority from U.S. patent application Ser. No. 60/326,311 filed on Oct. 1, 2001 and is a continuation-in-part of U.S. patent application Ser. No. 09/767,538 filed on Jan. 23, 2001 (pending) that claims priority from U.S. patent application Ser. No. 60/177,590 filed on Jan. 24, 2000.

FIELD OF THE INVENTION

The present invention generally relates to novel methods and arrays for detecting a plurality of proteins and more particularly to methods and arrays for detecting the expressions, activities and functions of multiple proteins.

BACKGROUND OF THE INVENTION

The availability of a large number of biological reagents, such as hundreds of thousands of cloned DNA sequences, numerous antibodies and recombinant proteins, millions of compounds obtained through combinatory chemical synthesis, has promoted the development of technologies that make use of these reagents in biological research, clinical diagnostics and drug development. Special position-addressable arrays of biological reagents have been designed, in which each of the reagents is placed at a pre-defined position so that it can be identified later by the position. For example, in a DNA array, a large number of cDNA or oligos are immobilized, each at a pre-defined position and can be identified later by that position. DNA arrays are used in large-scale hybridization assays for applications such as monitoring gene expressions (Schena et al., 1995, *Science* 270:467-470; DeRisi et al., 1996, *Nature Genetics* 14:457-460). Arrays of DNA clones in expression vectors are also used to express their encoded proteins in mammalian cells (Ziauddin and Sabatini, 2001, *Nature* 411, 107-110).

In a protein array, many proteins are immobilized on a support, each at a predetermined position so that it can be identified subsequently by this unique position. Two types of protein arrays are particularly useful: antibody arrays and recombinant protein arrays, which contain a plurality of antibodies and a plurality of recombinant proteins, respectively. Because antibody arrays are capable of binding cellular proteins, they are particularly useful in revealing protein in vivo activities. Therefore, the technology makes it possible to study the properties of a large number of cellular proteins in a single assay. Specifically, antibody arrays have been applied in studying in vivo protein-protein interactions, protein posttranslational modifications and protein expression patterns (U.S. Pat. No. 6,197,599).

In addition, arrays of cells, tissues, lipids, polymers, drugs and other chemical substances can be fabricated for large scale screening assays in medical diagnostics, drug discovery, molecular biology, immunology and toxicology (Kononen, et al., Nature Medicine, 4:844-7, 1998).

Proteins are important component of cells and they are the real players in various cellular processes; and they are the targets of most drugs. The entire human genome encodes about 40,000 proteins. Although a given cell may contain the DNA encoding all the proteins, it usually only expresses a fraction of them. A cell line usually expresses about 10,000 proteins and an even higher number is expressed in tissues. The protein expression pattern of a cell determines its shape and function; and abnormal protein expressions cause diseases. Therefore, one major task of proteomics is to identify the proteins expressed in a given source.

A protein (with an identical primary amino acid sequence) may be present in different forms in the cells largely due to posttranslational modifications. Since, in many cases, only special posttranslationally modified proteins are activated and directly involved in a cellular process, the detection of the presence of these activated proteins in the cells can provide valuable information on that cellular process.

There are many different protein posttranslational modifications such as phosphorylation, glycosylation, and ubiquitination. And they play important roles in regulating protein activities. Phosphorylation in either serine, threonine or tyrosine residues is an important mechanism in signal transduction. Aberrant protein phosphorylation contributes to many human diseases. Among the methods of detecting protein phosphorylations, metabolic labeling of cells with radioisotopes and immuno-detection with antibodies against phosphoproteins is most commonly used. However, these methods are usually only applicable to the analysis of one or a few proteins at a time. Although antibodies specific for phosphorylated amino acids, such as PY20 and 4G10, can reveal multiple phosphorylated proteins, they alone are unable to identify individual phosphorylated proteins. New methods for simultaneously detecting the presence of multiple phosphorylated proteins or other modified proteins are highly desirable for signal transduction studies and clinical diagnosis.

Quantification of protein expressions has applications in a variety of fields including biomedical research, disease diagnosis, identification of therapeutic markers and targets, and in profiling cellular responses to toxins and pharmaceuticals. In basic biomedical research, it is usually desirable to know what proteins are expressed in specific cells or under specific conditions. And by comparing the protein expression profiles between different cell types, it is possible to identify those proteins whose expressions and activations characterize a particular cell type. In many signal transduction pathways, certain proteins are specifically activated; and the detection of these active proteins, e.g., phosphorylated proteins, may provide important information on the activations of specific signal transduction pathways.

Many diseases alter protein expressions and in many cases abnormal protein expressions are the causes of the diseases. Therefore, determination of protein expression profiles and comparison of the expression profiles between normal and abnormal biological samples are useful for understanding disease mechanisms. Detecting the presence of proteins is also useful in clinical diagnostics. For example, examination of the presence of several viral proteins instead of just one in a blood sample is a more reliable diagnostic method for viral infections. Profiling proteins will be invaluable in distinguishing normal cells from early-stage cancers and also from malignant, metastatic cancer cells that are the real killers. In addition, protein expression profiling is useful in key areas of drug development, such as in drug target selection, toxicology and the identification of surrogate markers of drug response.

It has long been the goal of molecular biologists to develop technologies that can quantify, in a reliable and reproducible manner, the expression level of every individual protein and the different forms of each protein in a biological sample. However, this has turned out to be extremely difficult to achieve. Traditionally, the expression of one or a small number of proteins can be detected by immunological methods, such as western blotting and Enzyme-Linked Immunosorbent Assay (ELISA). Two-dimensional gel electrophoresis can be used to analyze the proteins expressed in a sample. However, it requires complicated procedures and it is necessary to determine the identities of the proteins displayed on the two-dimensional gel, which is difficult to achieve for most proteins. Recently, protein arrays are applied in studying protein expression patterns. In one strategy (U.S. Pat. No. 6,197,599; Haab, et al., *Genome Biol.* 2, research0004.1-0004.13, 2001), an antibody array is incubated with a protein sample and after incubation and washing, proteins specifically bound to their respective antibodies on the array are detected.

Immunochemical staining is a versatile technique in determining both the presence and localization of an antigen (Harlow and Lane, Antibodies, a laboratory manual, Cold Spring Harbor Press, 1988), which information is of immense value in biomedical research and clinical medicine. Most of the current methods, which employ the steps of incubating cells with an antibody solution, only allow cell staining with one or a few antibodies at a time. These methods are not suitable for applications in which the expressions and sub-cellular localizations of a large number of different proteins need to be examined. Therefore, a new method that is capable of staining cells with a large number of different antibodies is needed for such purposes.

SUMMARY OF THE INVENTION

It is an object of the invention to provide an array of biological reagents that enables one to maintain the positions of the reagents on the array support and yet allows the reagents to dissociate from the support when placed in contact with their interacting partners that are immobilized on another support.

It is also an object of the invention to provide methods of making and using the novel arrays of biological reagents for detecting, among other ligands, one or more proteins at one time. The preferred methods of invention are adapted to utilize various support materials and immobilization methods to make and use the arrays.

It is a further object of the invention to provide methods and arrays that enable one to use arrays of biological reagents to detect proteins and their properties, and more particularly, to detect and compare the presences and sub-cellular locations of one or more proteins in the cells.

The methods and arrays of the invention are designed to substantially expand the use of biological arrays in the field of detecting proteins and other biological molecules. For example, arrays of antibodies immobilized on a first, preferably solid, support are contacted with a protein sample immobilized on a second support so that one or more of the antibodies bind to their respective antigens and, after binding, the antibodies are then dissociated from the first support while maintaining association with their antigens on the second support.

A preferred method of the invention for detecting one or more biological molecules, generally comprises the steps of: providing a first support on which one or more reagents are immobilized; providing a second support on which one or more ligands are immobilized; contacting the reagents immobilized on the first support with the ligands immobilized on the second support whereby one or more of the reagents bind to one or more of the ligands; separating the first support from the second support; and detecting one or more reagents on said second support. The reagents are preferably immobilized on said first support with strength sufficient to immobilize said reagents in the contacting step and yet allow said bound reagents to dissociate from said first support in said separating step. The reagents immobilized on said first support may comprise one or more antibodies.

The ligands may be separated from each other before being immobilized on said second support using a variety of methods including, but not limited to: using gel electrophoresis based, at least in part, on their molecular weights; using gel electrophoresis based, at least in part, on their isoelectric points; using two-dimensional gel electrophoresis based at least in part on one or both of their molecular weights and isoelectric points; immunologically such as by using one or more antibody arrays. The reagents may be selected from a group consisting of antibodies, recombinant proteins, DNA, RNA, oligo nucleotides, carbohydrates, and small chemicals. The reagents may be immobilized at one or more predetermined positions on said first support. If the reagent selected is one or more antibodies, antibodies may be specific for post-translationally modified proteins such as phosphorylated proteins.

One or more of the reagents may be each immobilized at one or more predetermined positions on the support. The number of different kinds of reagents on any given support are preferably: 2 to 50; 5 to 100,000; 200 to 10,000; 50 to 1,000; 5 to 500; 5 to 100; and 5 to 50.

The first or second support may comprise materials selected from a group consisting of nitrocellulose, nylon, polyvinylidene difluordie, glass, or plastic, and their derivatives.

Another preferred method of the invention to detect one or more biological molecules in cells, generally comprises the steps of: (a) immobilizing one or more antibodies on a first support, wherein said antibodies are provided at predetermined positions on said first support such that said antibodies can be identified by the position where they are immobilized; (b) placing said cells on a second support; (c) contacting said antibodies on said first support with said cells on said second support to allow said antibodies to bind to any corresponding antigens in said cells; (d) separating said first support from said second support whereby one or more of said bound antibodies remain bound to the corresponding antigens after separation; (e) detecting said antibodies bound to antigens in said cells on said second support. The method may utilize cells that are immobilized on said second support, wherein said cells may comprise one or more tissue sections.

The antibodies may be specific for posttranslationally modified proteins such as phosphorylated proteins. The number of different kinds of reagents that can be immobilized at one or more predetermined positions may include 5 to 100, 000; 200 to 10,000; 50 to 1,000; 5 to 500; and 2 to 50. The supports may comprise materials selected from a group consisting of nitrocellulose, nylon, polyvinylidene difluordie, glass, or plastic, and their derivatives. Proteins such as antibodies may be immobilized on the supports in one or more shapes selected from a group consisting of circular, elongated, and polygonal.

The first or second support may comprise an array. The array may be made using various materials including, but not limited to, a plurality of whole or partial capillary tubes.

The antibodies may be immobilized on said support using one or more intermediaries selected from a group consisting of modified protein A and modified protein G. Protein A or protein G are modified to alter its binding affinity. One or more of said antibodies may have at least one constant region, that is adapted to engage one or more of the modified proteins, and at least one variable region that is available to bind to one or more antigens.

The step of detecting preferably comprises one or more steps of detecting selected from a group consisting of, determining whether one or more of said antibodies is present on one or both supports, identifying one or more locations of said antibodies after the separating step, determining one or more quantities of said antibodies, and identifying one or more types of antibodies.

Another preferred method of the invention for detecting one or more biological molecules comprises the steps of: (a) immobilizing one or more ligands on a second support; (b) immobilizing one or more reagents, that are adapted to interact with one or more of said ligands, on a first support; (c) contacting said reagents with said ligands to allow one or more of said reagents to bind with one or more of said ligands; (d) cross-linking one or more said reagents with one or more of said ligands; (e) separating said first support from said second support to allow one or more of said reagents that are bound to one or more of said ligands to dissociate from said first support; (f) detecting one or more of said reagents on said second support.

One or more of said ligands and said reagents may be cross-linked using, at least in part, one or more aldehydes which are preferably, but not necessarily limited to, formaldehyde and glutaldehyde.

A preferred embodiment of one of the arrays of the invention for use in detecting biological molecules, generally comprises: a first support adapted to at least temporarily immobilize one or more reagents and adapted to be placed in contact with a second support, to which one or more ligands are immobilized, so that one or more of said reagents is allowed to bind with one or more of said ligands and to subsequently dissociate from said first support and remain bound to said ligands on said second support.

The supports may comprise various materials, including, but not limited to, one or more of the following materials: nylon, nitrocellulose, polyvinylidene difluordie, glass, or plastic, and their derivatives. For example, the support may comprise one or more nylon membranes or a whole or a portion of one or more capillary tubes. One or more of said reagents are immobilized on a support may be immobilized in one or more shapes selected from a group consisting of circular, elongated and polygonal. The ligands may also be immobilized, at least in part, by covalent bonds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other objects, features and advantages will occur to those skilled in the art from the following description of the preferred embodiments and the accompanying drawings in which:

FIG. 4a shows the result after using a preferred method and array of the invention whereby A431 cells were stained with an array containing rabbit anti-YY1 antibodies (left in green), mouse anti-p130$^{cas}$ antibodies (middle in red), and both YY1 (right in green) and p130$^{cas}$ (right in red) antibodies at neighboring positions. Goat anti-rabbit Cy2-labeled secondary antibodies and goat anti-mouse Cy3-labeled secondary antibodies were used.

FIG. 4b is an enlarged view of the double staining of YY1 (green) and p130$^{cas}$ (red) shown in FIG. 4a.

DESCRIPTION OF THE PREFERRED EMBODIMENTS AND METHODS

Figure 1:
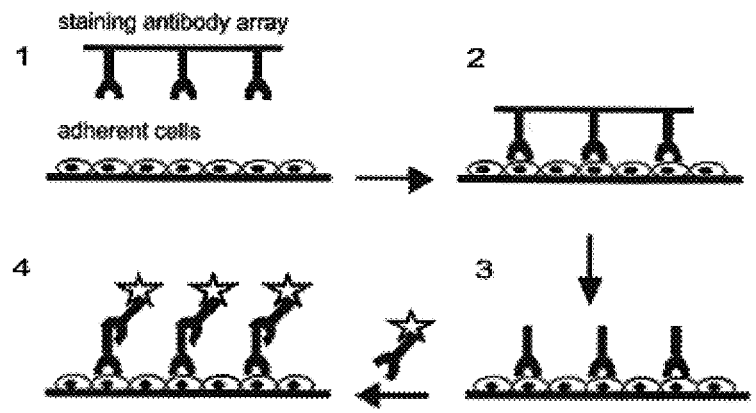
FIG. 1 is a schematic diagram of a preferred method of the invention for detecting multiple proteins.

The invention relates to novel arrays of biological reagents and methods for making and using the arrays. The method generally features the steps of providing a first support immobilized with one or more reagents, providing a second support immobilized with one or more ligands, contacting the reagents with the ligands whereby one or more of the reagents bind to the ligands, separating the supports after binding whereby the bound reagents remain bound to the ligands, and detecting and/or comparing various biological targets.

One of the methods allows for a reagent, immobilized on a solid support, to bind its interacting partner that is immobilized on another support. In particular, antibody arrays are made so that the immobilized antibodies can dissociate from the support after binding their respective antigens that are immobilized on a second support. The binding of each antibody-antigen occurs at a pre-determined position.

The term "reagents" as used herein refers to any molecules of biological interest, such as antibodies, recombinant proteins, synthesized peptides, DNA, RNA, nucleotides, and small chemicals.

The term "ligands" as used herein refers to any biological molecule that is interactive with one or more reagents.

The term "array" as used herein refers to a device that includes, but is not limited to, a solid support and a plurality of reagents or ligands. For example, antibodies may be immobilized on the support, each at a predefined position so that each antibody can be identified by a specific position on the support.

The term "immobilization" is used herein, means the restriction of a reagent on a support so that the movement of the reagent on the support is limited. For example, when an antibody is immobilized on a support, the antibody is attached to the support so that it may not dissociate from the support and the movement of the antibody on the support is also limited. However, under some conditions, as described in the invention, an immobilized reagent can dissociate from the support. The physical and chemical nature of the immobilization determines whether an immobilized reagent can dissociate from the support; and how efficient the dissociation will be.

The term "support" is used herein, for the purposes of the specification and claims, to mean the structure on which biological reagents are deposited and immobilized. In the preferred embodiments, the supports may be, but are not limited to, rigid plates (glass or plastics) or membranes made of nitrocellulose, nylon, polyvinylidene difluoride (PVDF), or their derivatives. Membranes are easier to handle and reagents can be readily immobilized on them. Glass or plastic plates provide rigid support and are necessary in some applications.

Preferably, the solid supports are pretreated so that biological reagents deposited on them can be immobilized with adequate strength suitable for specific applications. One way to treat the solid support is to coat it with a layer of polymers that in turn will interact with biological reagents through non-specific, non-covalent bonds. For example, polymers comprising polylysine or polyethyleneimine may be used to coat glass slides or coverslips for use in immobilizing biological molecules.

Several techniques are available for depositing and immobilizing a plurality of biological reagents on solid supports, such as those described by Lehrach, et al. (Hybridization fingerprinting in genome mapping and sequencing, genome analysis, Vol. 1, Davies and Tilgham, Eds, Cold Spring Harbor Press, pp. 39-81, 1990) and Brown et al. (U.S. Pat. No. 5,807,522). Each of the aforementioned articles is incorporated by reference in its entirety. For example, nanolitre volumes of antibodies in an aqueous solution can be printed on a glass slide using a robotic arrayer. Therefore, arrays of biological reagents may be formed by depositing a plurality of reagents onto a flat solid support, one or a few reagents at a time, and each reagent at a pre-defined position.

The immobilization of antibodies may be via adsorption (Trevan, 1980, Immobilized Enzymes: an introduction and their application in biotechnology. Wiley, Chichester). The adsorption forces involved may be nonspecific, hydrophobic or ionic interactions. Typically adsorbent materials used include, but are not limited to, clay, charcoal, hydroxyapatite, and most frequently, ion-exchange materials such as DEAE-Sephadex.

Entrapment is another way to immobilize antibodies (Trevan, 1980, Immobilized Enzymes: an introduction and their application in biotechnology. Wiley, Chichester). The entrapped antibodies are not attached to the polymer; their free diffusion is merely restrained. One commonly used matrix is a polyacrylamide gel. In one preferred embodiment, capillary tubes are used to facilitate arraying and immobilizing biological reagents. The term "capillary tube" is used herein, to mean any wholly or partially enclosed elongated structure capable of containing and supporting biological reagents. The capillary tubes may be made from materials such as plastics and glass, which preferably do not interfere with the properties of biological reagents. The heights of the capillary tubes may be varied from micrometers to meters. A biological reagent is usually filled into a capillary tube as liquid solution. After filling, the reagent solution becomes solidified and the reagent is immobilized. The strength of immobilization may be varied depending on a given application.

Reagents are immobilized on a solid support directly or indirectly. For example, reagents may be directly deposited at high density on a support, which can be as small as a microscopic slide. Similar technology was developed for making high density DNA microarray (Shalon et al., Genome Research, 1996 Jul; 6(7): 639-645). Reagents may also be immobilized indirectly on the support. For instance, protein A or protein G, or their mutants can be first printed on a support as intermediates. Antibodies are then immobilized on the support through their interactions with protein A or G. One advantage of this method is that, by engaging the constant regions of antibodies with protein A or G, the variable regions of the antibodies (antigen-binding domains) will be fully exposed and available to bind antigens. Another advantage is that, since protein A or G can be modified to change their binding affinity for antibodies, when carefully designed mutants of protein A or protein G are used, antibodies can be immobilized on the support with desired strength. As such, antibodies on one hand can be immobilized on the support without losing positional information but on the other hand can leave the support and bind to other ligands of higher affinity. Recombinant fusion proteins can be immobilized through the interactions between their tags and the ligands attached on the support. For example, ligands (e.g., glutathione or nickel) can be first covalently attached on a support and then recombinant fusion proteins containing a tag (e.g., GST or 6×His) are immobilized on the same support via interacting with the ligands. The tags and ligands can be modified to change their affinities so that the immobilization will have desired strength.

Antibodies are usually deposited on a support as circular dots. However, antibodies can also be deposited in other shapes. For example, antibodies can be immobilized in an elongated shape, such as a rectangular shape of a few microns to a few centimeters wide and a few microns to a few centimeters long. Antibodies immobilized in such a shape can be used to bind antigens after separation according to a variety of methods.

An antibody specific for an antigen may be immobilized at a specific position on a support. In general, antibodies are immobilized at positions that when they make contacts with protein samples, each antibody will make contact with its own antigens. Therefore, a specific antibody may be immobilized at a specific position which is determined by the position of its antigen. For example, when antigens are first separated by two-dimensional gel electrophoresis and transferred and immobilized on a support; each antigen is immobilized at a specific position determined by its molecular weight and isoelectric point. Therefore, each of the antibodies can be immobilized according to the position of the antigen on the support.

The term "protein sample" as used herein refers to a variety of proteins and protein mixtures. For example, it can be a lysate from a cell line or tissue. Or it can be intact cells, or cells fixed on a support. A protein sample can be from different sources such as, but not limited to, cultured cell lines, human or animal tissue, or blood.

In one preferred embodiment, protein samples are cultured cells or tissue sections that can be placed on glass slides and immobilized. Before use, the cells can be fixed and permeabilized to expose proteins. The fixed cells retain certain cell morphology and most proteins stay at their original cellular positions. There are multiple methods for fixing and permeabilizing cells and tissues (Harlow and Lane, Antibodies, a laboratory manual, Cold Spring Harbor Press, 1988.). A commonly used fixation solution is a formaldehyde or glutaldehyde solution. Another commonly used fixation solution contains methanol instead.

Suspension cells, such as lymphocytes can be spun down on a support and immobilized on it. They may also be embedded in a medium, such as paraffin, collagen, gelatin, and then sectioned and placed on a support. Many known methods are available to prepare cell samples (Jones, T. C, Ward, J. M., Mohr, U. and Hunt, R. D. (editors), 1990, Hemopoietic System. Berlin, Springer-Verlag; Polak, J. M. and Van Noorden, S., 1997, Introduction to Immunocytochemistry. New York, Springer).

In another preferred embodiment, protein samples are prepared from cells or tissues by lysis. A typical lysis buffer contains detergents such as sodium dodecyl sulphate (SDS), Triton X-100, etc. The immobilization of protein samples can be via covalent or non-covalent bond and methods for immobilization are known in the arts. The size of the area on which a protein sample is immobilized on the support may be different depending on applications and the volume and amount of the protein sample immobilized. For example, when a membrane is used as support, if the binding capacity of the membrane is 10 mg protein per square centimeter, then up to 10 mg of protein lysate can be immobilized on a membrane with a size of 1 square centimeter.

The protein lysates may be evenly placed on a support and immobilized on it. However, for other applications, proteins may be first separated and then immobilized on a support. Many methods for protein separations are known in the art. For example, proteins can be separated by one-dimensional sodium dodecyl sulphate-polyacrylamide gel electrophoresis (SDS-PAGE) according to molecular weight; or separated by 2-dimensional electrophoresis according to both molecular weight and isoelectric point. After separation by electrophoresis, proteins can be transferred and immobilized on a support.

In another preferred embodiment, protein samples can be separated by immunological methods, such as separation by an antibody array. A protein sample is first incubated with an antibody array on a first support to allow antibodies to capture and therefore separate their antigens present in the protein sample. After washing away non-binding proteins, the proteins captured at each position are dissociated from the antibodies and transferred onto a second support and immobilized on it. The interactions between antibodies and the first solid support can be much stronger than the interactions between antibodies and antigens. Therefore, conditions may be found to disrupt antibody-antigen interactions but leave antibody immobilization on the first support intact. Under such conditions, the antigens but not the antibodies may be transferred onto the second support and immobilized on it. To avoid antibody dissociation from the first solid supports, the antibodies may be covalently immobilized on the supports.

In a typical transfer, the first support containing the antibodies and the antigens is contacted with a second support. Then they are placed in a buffer solution that could disrupt the interactions between the antigens and antibodies. And at the same time, an electric current is applied so that the disassociated proteins will move from the first support to the second support. After completion the two supports are separated. The transfer and immobilization may take place simultaneously (proteins are transferred and immobilized at the same time) or sequentially (proteins are transferred first and then immobilized). And if the immobilization is not as strong as desired the proteins could be further immobilized, e.g., through covalent bond. Methods are known in the art for covalent immobilization of proteins on solid support.

Once prepared, the protein samples are contacted with another antibody array. The contact is preferably carried out so that each antibody contacts its respective antigen to allow for specific binding. The antibodies on this array are dissociable from the support. Therefore, after separation of the antibody array support and the protein sample support, antibodies that bond to the antigens will be present on the sample support. By detecting the antibodies, the presence and abundance of antigens in the sample are detected.

Some of the methods are adapted to allow antibodies immobilized on one support to bind antigens immobilized on another support. In one preferred method, antibodies immobilized on one support are allowed to interact with antigens immobilized on a second support by placing the two supports together to make contact. After incubation for a certain time, the two supports are separated. Depending on the interactions between antibodies and antigens, some antibodies will dissociate from the first support and bind to the second support where antigens are immobilized. The strength of antibody immobilization on the first support is preferably weaker than the interactions between antibodies and antigens, and weaker than the strength of the immobilization of antigens on the second support. Conditions such as an electric field can be applied to facilitate the dissociation of the antibodies from the support.

After the binding of antigen and antibodies, the antigen-antibody complexes can be stabilized using covalent cross-linking. The cross-linking is preferably performed in such a way that antibody-antigen complexes are cross-linked but the antibodies are not cross-linked on their support. This can be achieved by choosing specific cross-linkers and special support for antibodies. There are hundreds of known cross-linkers and a variety of methods have been developed to use them to cross-link proteins (Wong, Shan S., Chemistry of protein conjugation and cross-linking. Boca Raton: CRC Press, 1993). For example, commonly used cross-linkers include aldehydes such as, but not limited to, formaldehyde and glutaldehyde.

The antibodies bound to the antigens are then detected. Many known arts can be used to detect antibodies. A common method is to use enzyme-conjugated secondary antibodies, such as horseradish peroxidase or alkaline phosphatase conjugated goat anti-rabbit and goat anti-mouse antibodies. Fluorescent-labeled secondary antibodies can also be used. Other technologies that can be used include immuno-PCR (Sano et al., 1992, *Science* 258, 120-122), rolling circle DNA amplification technique (Schweitzer et al., 2000, *Proc. Natl. Acad. Sci. USA* 97, 10113-10119), and immuno-detection amplified by T7 RNA polymerase (Zhang et al., 2001, *Proc. Natl. Acad. Sci. USA*, Vol. 98, 5497-5502.).

In one preferred embodiment of the arrays of the invention, arrays of antibodies may be used to stain cells, which is shown schematically in FIG. 1. Cells can be seeded on a coverslip, cultured, fixed and permeabilized to expose the antigens. Cell preparations are then incubated with an antibody array to allow the antibodies to bind to their respective antigens. After binding, the antibody array support and the cell support are separated. Some of the antibodies will be transferred to the cell support due to their interactions with their antigens. The amount of the bound and transferred antibodies will be related to the amount of antigens present in the cells.

By detecting the presence and quantities of the antibodies trapped on the cell support, the presence and quantities of their antigens in the cells can be determined. If the antibodies are conjugated with an enzyme, they can be revealed by enzymatic reactions. Alkaline phosphatase is commonly used and known substrates will give insoluble color products after reaction. In addition, if the antibodies are labeled with fluorescent molecules, they may also be observed directly under fluorescent microscopy. In many cases fluorescent- or enzyme-conjugated secondary antibodies can be used to reveal the presences of the primary antibodies.

For the purpose of revealing the presences and quantities of the antigens, the staining may simply be observed at a low magnification. However, to reveal other properties of the antigens, such as their sub-cellular localizations, the staining is preferably observed at a higher magnification.

Simultaneous staining of two proteins (double staining) is a unique tool for studying two functionally related proteins. For example, evidence of protein interactions often includes the demonstration that the proteins co-localize in the same cellular structure. Two or more antibodies can be immobilized on the same position of the antibody array so that two or more antigens can be detected at the same location simultaneously.

DNA probes instead of antibodies may be arrayed and used to detect the presence of specific DNA or RNA in the cells. To do so, DNA or RNA probes are immobilized on a solid support. Preferably, the immobilization of the probes is strong enough to maintain probes' positions on the support; but are preferably weaker than the interactions between the probes and their targets, so that when the probes bind to their targets, the probes can dissociate from the support. This method has many advantages over in situ hybridization, which usually only detects one or a few DNA or RNA sequences. When an array of DNA or RNA probes made according to the present invention is used, the presence and locations of a large number of DNA or RNA sequences can be detected in morphologically preserved tissue sections or cell preparations, each at a pre-defined position. The methods for preparing DNA and RNA probes, to be arrayed on a support, and the methods for preparing tissues or cells are known in the art (Ian A. Darby (Editor), In Situ Hybridization Protocols (Methods in Molecular Biology, 123), by Humana Press; ISBN: 0896036863; 2nd edition, 2000).

In another preferred embodiment, an antibody array is used to detect proteins in a protein lysate. To do so, an antibody array immobilized on a first support is incubated with a protein lysate immobilized on a second support. After incubation for certain time, the antibodies will bind their respective antigens in the lysate that are immobilized on the second support. Then the first support is separated from the second support. Under proper conditions, the antigen-bound antibodies will be dissociated from the first support and stay on the second support, on which their antigens are immobilized. The amount of an antibody transferred to the second support will be proportional to the abundance of its antigens in the protein lysate. Therefore, the detection of the amount of antibodies on the second support will reveal the abundance of their antigens in the protein sample.

In many applications, proteins can be first separated and/or concentrated, which may be necessary to detect low abundant proteins. In one embodiment, proteins are first separated by one-dimensional SDS/PAGE and transferred to a membrane support so that each protein is immobilized on the support at the position determined by its molecular weight. Then the lysate membrane is contacted with an antibody array, in which antibodies are immobilized in elongated shapes at specific positions, so that each of the antibodies will be able to contact its antigen at the specific position determined by the molecular weight of that antigen.

Proteins may also be separated by two-dimensional gel electrophoresis and transferred to a support such as a polyvinylidene difluoride (PVDF) membrane. Then the lysate membrane is contacted with an antibody array, which may contain multiple antibodies that each may be immobilized at a predetermined position so that each antibody will contact its corresponding antigen.

Proteins may also be separated and concentrated by immunological methods. One way to achieve this is to use antibody arrays. For example, a first antibody array can be incubated with a protein sample so that the proteins are captured and separated by each antibody immobilized on the array. The antibodies in this first array are preferably strongly immobilized, e.g. via covalent bond. Then the antigens are dissociated from the antibodies and transferred and immobilized on a second support. This process can be performed with several known methods. A second antibody array is then used to detect the antigens. Antibodies on the second array are immobilized in such a way that after binding their respective antigens, antibodies can be dissociated from the array support. Antibodies in the first and second arrays against the same antigen may be immobilized at corresponding positions; and they can be identical or different.

EXAMPLES

The following examples are for illustration only and in no way are intended to limit the present invention. Although the examples describe the use of antibody arrays according to the invention, similar usage for arrays of biological reagents other than antibodies are obvious to the people familiar with the arts. Such arrays of biological reagents include but are not limited to arrays of recombinant proteins, recombinant antibodies, single chain antibodies, nucleic acids, oligos, cDNA probes, carbohydrates, lipids, small chemicals. For example, an array of immobilized cDNA probes can be used in in situ hybridization to reveal the expressions of multiple mRNA in cells.

Example 1

Making of Antibody Arrays

Antibodies from commercial sources (about 0.5 μg/μl) were arrayed on Nylon membranes (from Amersham Life Science) using a robotic arrayer. About 40 ng antibodies in 80 nl solutions were deposited at each spot using a 0.6 mm solid pin, spaced 600 μm apart. Antibodies were immobilized by non-covalent bonds between nylon membranes and the antibodies. Antibody arrays were either used immediately or stored at 4° C. for less than 48 hrs before use.

Example 2

Use of Antibody Array in Immunochemical Staining

This example is to demonstrate the use of antibody arrays prepared by the method disclosed for immunochemical staining. Antibody arrays made in Example 1 with 200 antibodies against different cellular proteins were used.

Figure 2:
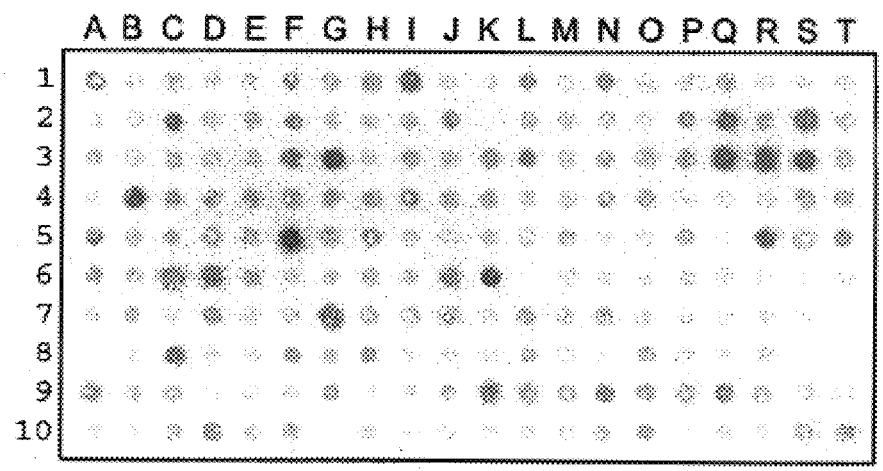
FIG. 2 shows the result after using a preferred method and array of the invention to detect multiple proteins. In this example, MDCK cells were stained with an array of 200 antibodies. The staining was observed via alkaline phosphatase-mediated color reaction with BCIP/NBT as substrates.

Madin Darby Canine Kidney (MDCK) cells were seeded on a culture dish and cultured for 2 days until confluence. Then they were fixed and permeabilized in Methanol/Acetone (1:1) for 10 min at −20 degree. After rinsing with phosphate-buffered saline (PBS), MDCK cells were contacted with an antibody array for about 1 hour. During the incubation the antibodies bound their antigens present in the cells. After that, antibody array support and cell support were separated. Cells were rinsed with phosphate-buffered saline again and alkaline phosphatase-labeled secondary antibodies were added for half an hour. After wash, the staining was visualized by color reaction with 5-bromo-4-chloro-indolyl-phosphatase (BCIP) and nitroblue tetrazolium (NBT) as substrates. The enzymatic reaction was stopped by washing off substrates with PBS and the image was obtained by scanning with a flat-bed scanner (FIG. 2). Cells at many positions were stained with antibodies and there was little mixing of the antibodies, as judged by the lack of staining at the areas between immobilized antibodies. The regular pattern of the stained spots matches the pattern in which the antibodies were printed.

Example 3

Use of Antibody Array in Fluorescent Immunochemical Staining

Figures 3A, 3C, 3E, 3G:
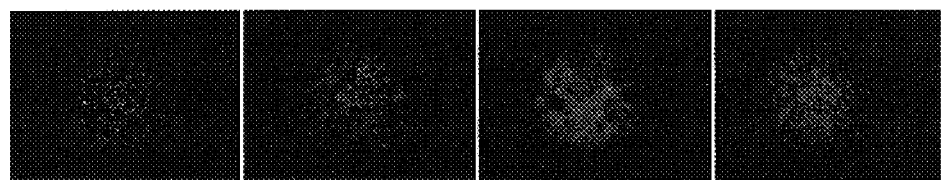
FIG. 3a shows the result after using a preferred method and array of the invention using fluorescent staining. An array of 200 rabbit polyclonal antibodies was used and the staining of protein IRF1 at one position is shown here at a scale bar of 300 µm.
FIG. 3c shows the result after using a preferred method and array of the invention using fluorescent staining. An array of 200 rabbit polyclonal antibodies was used and the staining of signaling molecule 14-3-3 β at one position is shown.
FIG. 3e shows the result after using a preferred method and array of the invention using fluorescent staining. An array of 200 rabbit polyclonal antibodies was used and the staining of cell adhesion protein β-catenin at one position is shown.
FIG. 3g shows the result after using a preferred method and array of the invention using fluorescent staining. An array of 200 rabbit polyclonal antibodies was used and the staining of transcriptional factor Ets-1 at one position is shown here.
Figures 3B, 3D, 3F, 3H:
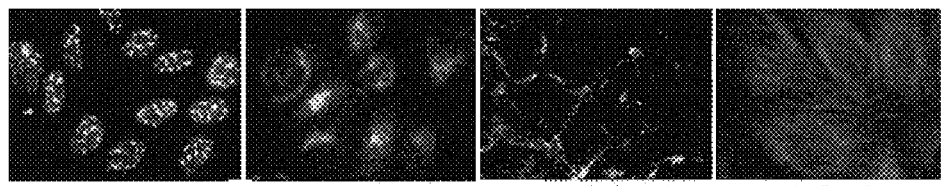
FIG. 3b is a partial, enlarged view of the image in FIG. 3a at a scale bar of 30 µm.
FIG. 3d is a partial, enlarged view of the image from FIG. 3c.
FIG. 3f is partial, enlarged view of the image from FIG. 3e.
FIG. 3h is a partial, enlarged view of the image from FIG. 3g.

In this example, about 5 ng antibodies in 10 nl solutions were deposited at each spot on Nylon membrane using a 0.3 mm solid pin, spaced 300 μm apart between neighboring spots. Then the antibody array was used to stain A431 cells by the method represented schematically in FIG. 1 and described in Example 2, except that fluorescent-labeled secondary antibodies were used and the staining was observed under fluorescent microscope (FIG. 3). A low magnification observation under fluorescent microscopy showed that each staining spot is about 300-μm in diameter and consists of a cluster of 400 cells (FIG. 3a, 3c, 3e, and 3g). There are clear boundaries between the stained areas and non-stained areas. A high magnification observation revealed the detailed staining patterns, e.g., nuclei localization of IRF1 (FIG. 3b), cytoplasmic staining of 14-3-3β (FIG. 3d) and Ets-1 (FIG. 3f), and cell-cell contacts staining of beta-catenin (FIG. 3h). The staining is indistinguishable from that obtained with standard immunostaining procedure.

Example 4

Antibody Arrays Made in Capillary Tubes

This example is to use antibody arrays made with capillary tubes to stain cells. Each antibody was mixed with low-melting agarose solution and injected into a plastic capillary tube of 1-cm high, 2-mm in outer diameter and about 0.2 mm thick. After the gel became solid, capillary tubes were bundled together and cut across section to produce arrays of about 1-mm high.

Then the antibody array was placed on a glass support and contacted with cells fixed on another glass support to allow the binding of antibodies to their antigens. Antibodies that bound to the antigens were detected with fluorescent-labeled secondary antibodies and observed under microscope as in Example 3.

Example 5

Antibody Arrays Made in Capillary Tubes for Fluorescent Immunostaining

Fluorescent-labeled antibodies were first mixed with a low-melting agarose solution at high temperature and then the antibody solutions were injected into capillary tubes to make a capillary array. Temperature was lowed to solidify the solutions in the capillary tubes. The tubes were then cut to make thin arrays; less than 1 mm high; and put on a plastic solid support and glued on it. The array was contacted with fixed cells which were placed on a cover glass to allow antibodies to contact antigens. Then the cells and antibody array were incubated at 37° C. for 2 hrs. After that, temperature was lowed and the array and cells were separated. Cells on the cover glass were then washed with PBS and observed under microscope.

Example 6

Use of Antibody Arrays in Double Staining

Figures 4A, 4B:

An antibody array was made that had 100 spots; each spot contained one or two antibodies. At the spots where two different antibodies were immobilized, one of them was mouse monoclonal and the other one was rabbit polyclonal. The array was used to stain A431 cells seeded on a cover glass. After staining, A431 cells were incubated with Cy2-labeled goat anti-rabbit secondary antibodies and Cy3-labeled goat anti-mouse secondary antibodies. The presence and locations of the antigens were examined by fluorescent microscopy (FIGS. 4a and 4b). At the positions where two antibodies were present, the two corresponding antigens were observed. The two antibodies/antigens can be distinguished by different labeling and different cellular localizations. For example, in FIG. 4 the nuclear localization of protein YY1 and membrane localization of protein p130$^{cas}$ were seen individually (FIG.4a, left and middle) and together (FIG. 4a, right; and FIG. 4b).

Example 7

Figure 5:
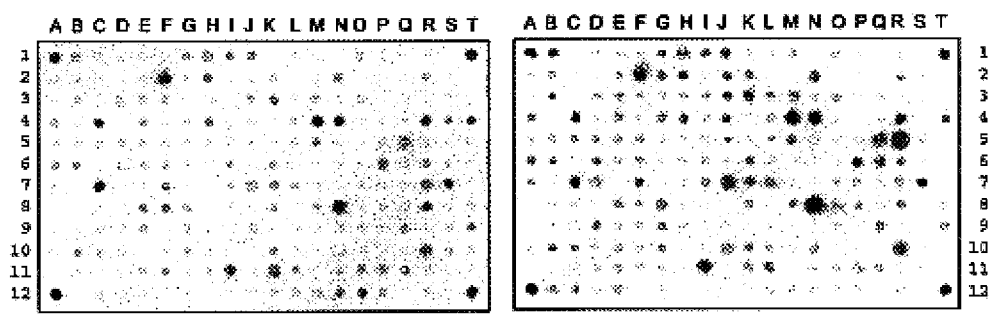
FIG. 5 shows the result after using a preferred method and array of the invention to detect protein expressions in two biological samples. Protein expressions in ME180 cells are shown at left and protein expressions in A431 cells are shown at right. Antibody arrays with 240 antibodies were used in this example. The staining was observed via alkaline phosphatase-mediated color reaction with BCIP/NBT as substrates.
Figure 6:
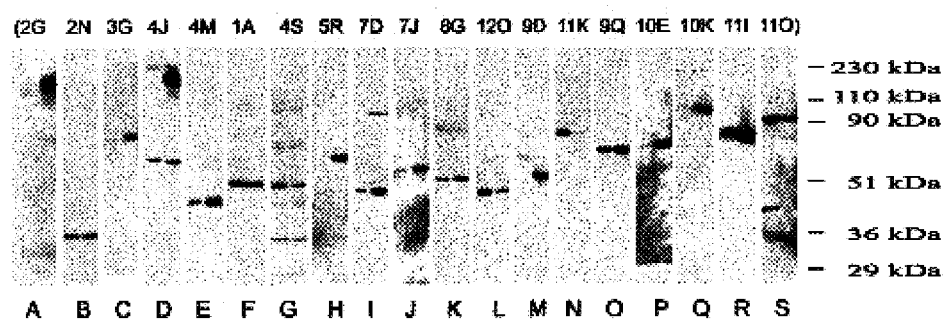
FIG. 6 shows the result using Western blotting to determine the differences in protein expression as detected in FIG. 5. Expressions of 19 proteins in ME180 cells (left lanes) and in A431 cells (right lanes) as detected by Western blotting are shown here. Proteins examined are: A, Cb1 (120 kD); B, Cdc2 (34 kD); C, Cortactin (80 kD); D, Neu (185 kD); E, ERK1 (44 kD); F, Ets-1 (51 kD); G, GSK-3α (51 kD); H, HSP 70 (70 kD); I, JNK1 (46 kD); J, Lyn (56 kD); K, NFκB p50 (50 kD); L, Skp2 p45 (45 kD); M, p53 (53 kD); N, Plk3 (70 kD); O, SH-PTP2 (60 kD); P, Raf-1 (74 kD); Q, Rb p107 (107 kD); R, Stat1 (84 kD); S, Stat5a (95 kD). The corresponding position for each of the antibodies in FIG. 5 is indicated on the top. Protein lysates of A431 and ME180 cells occupying equal culture areas were loaded in each lane.

Use of Antibody Array Staining to Compare Protein Expressions Between Cell Samples Antibody arrays containing both mouse monoclonal and rabbit polyclonal antibodies against 240 proteins involved in various signaling pathways were produced as described in previous examples. And the presence of the 240 proteins were detected and compared between A431 cells, and ME180 cells, two human cancer cell lines that are widely used in research. The result showed that the two cell samples have very different protein expression patterns. Many of the 240 target proteins are expressed differently in A431 and ME180 cells (FIG. 5). For example, A431 cells express more Cbl, cortactin, Neu, HSP 70, JNK1, p53, Raf-1, and Stat1; but less GSK-3α, Skp2 p45, Plk3, and Stat5a than ME180 cells. The expressions of these proteins were also examined by Western blotting (FIG. 6). And the results obtained with the two methods correlated well, suggesting that antibody array staining is a valid method for profiling protein expressions.

Example 8

Detecting Pathway Activation With Antibody Arrays

Antibodies that are specifically against activated proteins (phosphorylated proteins) were used to make antibody arrays and the arrays were used to examine the presence of these activated proteins in a biological sample. The presence of activated proteins suggested that certain signal transduction pathways were activated in the sample.

Example 9

Detection of Specific Proteins in a Protein Lysate

In this example, 50 μg bacterial lysate containing Stat1 recombinant protein was immobilized on a 1-square-centimeter nitrocellulose membrane. Then the lysate membrane was contacted with an antibody array, which contains multiple antibodies including Stat1 antibodies on a nylon membrane.

After 1-2 hr incubation, some antibodies bound their respective antigens in the lysate. When the lysate membrane and antibody array were physically separated, some antibodies were dissociated from the antibody array support and bound to the lysate support due to their interactions with antigens. The amount of an antibody bound to the lysate slide depends on the abundance of the antigen present in the lysate. Antibodies were detected with HRP-conjugated secondary antibodies and visualized through enhanced chemiluminescence (ECL) reaction.

Example 10

Detection of Stat1 Protein With HRP-Conjugated Primary Antibodies

This example is similar to Example 9 except that horseradish peroxidase (HRP)conjugated stat1 primary antibodies were used so that enzyme-conjugated secondary antibodies were not needed for the detection.

Example 11

Staining With Antibody Array Immobilized Via Protein A Mutant

In this example, a recombinant protein A mutant with one antibody binding domain was first immobilized on a support; and then HRP-conjugated antibodies were immobilized on the support via interaction with the protein A mutant to form an antibody array. Such made antibody array was contacted with a protein lysate immobilized on another support. After 1 hr incubation, the antibody array was removed and the antibodies bound to the protein sample support were detected via ECL reaction.

Example 12

Separation of Protein Samples By SDS/PAGE

Figure 7:
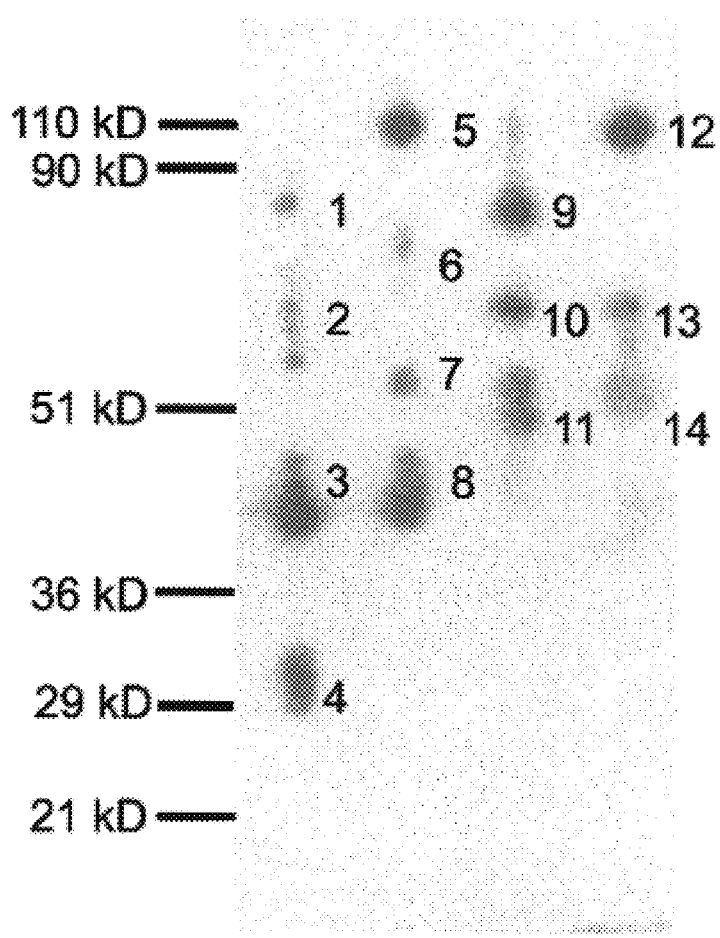
FIG. 7 shows the results after using a preferred method and array of the invention to detect protein expressions in a protein lysate of A431 cells separated by SDS/PAGE. Antibodies against 12 proteins were immobilized at proper positions. Proteins examined are: 1, IKK beta; 2, E2F1; 3, ERK2; 4, 14-3-3; 5, Rb p107; 6, ERK1 control (antibodies were immobilized at positions where there was no antigen); 7, Ets-1; 8, ERK1; 9, Stat1; 10, 14-3-3 control; 11, JNK1; 12, Stat2; 13, Lyn; 14, p38. The corresponding position for each of the antibodies is indicated at the right of the corresponding spot.

In this example, protein lysates of A431 cells were separated by SDS/PAGE using a curtain gel and transferred to a PVDF membrane. Antibody arrays containing 12 antibodies against well-studied proteins were made using nylon membrane as support and used in the assay. The antibodies were immobilized in rectangular shapes and were carefully positioned on the array so that when the arrays made contacts with the protein lysate immobilized on the PVDF membrane, antibodies can bind their respective antigens. After binding between antibodies and antigens, nylon membrane support was removed from the PVDF membrane. The antibodies that attached on the PVDF membrane via interactions with respective antigens were detected using HRP-conjugated secondary antibodies and revealed by ECL reaction. As shown in FIG. 7, several antigens were detected as expressed in A431 cells. And they are detected on the PVDF membrane at positions of expected molecular weights. Antibodies intentionally immobilized at wrong positions gave lower signals, suggesting that the method is valid for profiling protein expressions.

Example 13

Separation of Protein Samples By Two-Dimensional Gel Electrophoresis

This example is similar to Example 12 except that proteins were separated by two-dimensional gel electrophoresis and transferred to a polyvinylidene difluoride (PVDF) membrane. Then the lysate membrane was contacted with an antibody array, which contained multiple antibodies and each of them was immobilized at a predetermined position so that each antibody would contact with its antigen.

Example 14

Separation of Protein Samples by Antibody Arrays

In this example, proteins are first separated and concentrated by antibody arrays. An antibody array was made by immobilizing antibodies on a support covalently; then the array was incubated with a protein sample so that the proteins were captured and separated by each antibody immobilized on the array. Then the antigens were dissociated from the antibodies and transferred and immobilized on a sample support. Because the antibodies were covalently immobilized, no or very littler was transferred to the sample support. A second antibody array was then made in such a way that antibodies against the same antigen were at the same relative positions as the antibodies were in the first antibody array. When the second antibody array contacted the sample support on which antigens were immobilized, each of the antibodies made contact with respective antigen and bound to it. After binding, the array was separated from the sample support. Because some antibodies bound their antigens, they dissociated from the array support and bound to the sample support.

Although specific features of the invention are shown in some drawings and not others, this is for convenience only as some feature may be combined with any or all of the other features in accordance with the invention. Other embodiments and modifications will occur to those skilled in the art and are within the following claims:

What is claimed is:

1. A method for staining cells to detect one or more biological molecules in said cells, comprising the steps of:
   immobilizing a plurality of antibodies on a first support, wherein each of said antibodies is provided at predetermined positions on said first support such that each of said antibodies can be identified by the position where it is immobilized;
   (b) placing said cells on a second support;
   (c) fixing said cells with a fixation solution;
   (d) contacting said antibodies on said first support with said cells on said second support to allow said antibodies to bind to any corresponding interacting biological molecules in said cells;
   (e) separating said first support from said second support whereby one or more of said bound antibodies remain bound to the corresponding biological molecules after separation;
   (f) detecting said biological molecules by detecting said antibodies bound to said biological molecules in said cells.

2. The method of claim 1, wherein said fixation solution comprises chemicals selected from the group consisting of formaldehyde, glutaldehyde, acetone and methanol.

3. The method of claim 1, wherein said cells are one or more tissue sections.

4. The method of claim 1, wherein one or more of said antibodies are specific for one or more posttranslationally modified proteins.

5. The method of claim 1, wherein one or more of said antibodies are specific for one or more phosphorylated proteins.

6. The method of claim 1, wherein 5 to 100,000 different kinds of antibodies are each immobilized at one or more predetermined positions on said first support.

7. The method of claim 1, wherein 200 to 10,000 different antibodies are each immobilized at one or more predetermined positions on said first support.

8. The method of claim 1, wherein 50 to 1,000 different antibodies are each immobilized at one or more predetermined positions on said first support.

9. The method of claim 1, wherein 5 to 500 different antibodies are each immobilized at one or more predetermined positions on said first support.

10. The method of claim 1, wherein 5 to 100 different antibodies are each immobilized at one or more predetermined positions on said first support.

11. The method of claim 1, wherein 5 to 50 different antibodies are each immobilized at one or more predetermined positions on said first support.

12. The method of claim 1, wherein said first support comprises materials selected from the group consisting of nitrocellulose, nylon, polyvinylidene difluordie, glass, plastic, and their derivatives.

13. The method of claim 1, wherein said first support comprises materials selected from a- the group consisting of nylon and its derivatives.

14. The method of claim 1, wherein said reagents are immobilized on said first support in one or more shapes selected from the group consisting of circular, elongated, and polygonal.

15. The method of claim 1, wherein said first support comprises an array.

16. The method of claim 15, wherein said array comprises a plurality of whole or partial capillary tubes.

17. The method of claim 1, wherein said step of immobilizing said antibodies comprises the steps of, applying one or more intermediates to said first support; and applying one or more of said antibodies to said first support so that one or more of said antibodies interacts with one or more of said intermediates.

18. The method of claim 1, wherein said step of detecting comprises the one or more steps of detecting selecting from the group consisting of, determining whether one or more of said antibodies is present on one or both supports, identifying one or more locations of said antibodies after the separating step, determining one or more quantities of said antibodies, and identifying one or more types of antibodies.

19. The method of claim 1, wherein said antibodies are immobilized on said first support in circular shape.

20. The method of claim 1, wherein said step of immobilizing said antibodies comprises the step of applying one or more of said antibodies to said first support.

21. The method of claim 1, wherein said step of detecting comprises the step of determining the quantities of one or more of said antibodies.

* * * * *